(12) United States Patent
Su et al.

(10) Patent No.: US 8,088,479 B2
(45) Date of Patent: Jan. 3, 2012

(54) APPARATUS FOR INDICATING THE PASSAGE OF TIME, COMPOSITION AND FORMING METHOD THEREOF

(75) Inventors: Wei-Fang Su, Taipei (TW); Yulia Galagan, Taipei (TW); Sheng-Hao Hsu, Taipei (TW)

(73) Assignees: Wei-Fang Su, Taipei (TW); Sun Own Industrial Co. Ltd., Chang Hua Hsien (TW)

( * ) Notice: Subject to any disclaimer, the term of this patent is extended or adjusted under 35 U.S.C. 154(b) by 1064 days.

(21) Appl. No.: 11/949,536

(22) Filed: Dec. 3, 2007

(65) Prior Publication Data
US 2008/0138614 A1    Jun. 12, 2008

(30) Foreign Application Priority Data

Dec. 8, 2006   (TW) .............................. 95145956 A

(51) Int. Cl.
    *G11B 11/105* (2006.01)
(52) U.S. Cl. ....... 428/332; 426/392; 426/394; 428/35.7; 428/64.1; 428/64.4; 428/64.8; 428/339
(58) Field of Classification Search .................. 426/392, 426/394; 428/35.7, 64.1, 64.4, 64.8, 339, 428/332
See application file for complete search history.

(56) References Cited

U.S. PATENT DOCUMENTS

| | | | | | |
|---|---|---|---|---|---|
| 4,812,053 | A | * | 3/1989 | Bhattacharjee | ............... 374/102 |
| 5,057,434 | A | * | 10/1991 | Prusik et al. | ...................... 436/2 |
| 5,316,949 | A | * | 5/1994 | Bull et al. | ......................... 436/5 |

* cited by examiner

*Primary Examiner* — Terressa Boykin
(74) *Attorney, Agent, or Firm* — WPAT., P.C.; Justin King

(57) ABSTRACT

The present invention discloses an apparatus for indicating the passage of time, comprising a substrate and an indicating layer formed on the substrate. The indicating layer comprises a polymer matrix and a predetermined amount of redox compound under the reduced form. The redox compound is dispersed in the polymer matrix and has the following properties: the reduced form of the redox compound reacts with oxygen to form the oxidized form of the redox compound; the hue or color density of the reduced form of the redox compound is different from that of the oxidized form of the redox compound; and the hue or color density of the indicating layer varies as the time for the reduced form of the redox compound contacting with oxygen in environment increases to have the amount of the oxidized form of the redox compound increase so as to indicate the passage of time.

21 Claims, 3 Drawing Sheets

Fig. 2

APPARATUS FOR INDICATING THE PASSAGE OF TIME, COMPOSITION AND FORMING METHOD THEREOF

BACKGROUND OF THE INVENTION

1. Field of the Invention

The present invention is generally related to a time-indicating apparatus, and more particularly to an apparatus for indicating the passage of time, composition and forming method thereof.

2. Description of the Prior Art

Generally, food is considered to be safe within the shelf life. However, it is generally not true. For instance, the temperature of the environment for storing food is so high or the time of the food exposing to air is so long to result in bacterial overgrowth or food spoilage and thereby to affect human health. In order to avoid consumers from eating spoiled food, new packaging technology to indicate the state of food has been researched by various companies and academic organizations. For example, a time-temperature indicator (TTI) has a function of indicating the temperature and time variations of a product (such as food) undergoing the processes of storage, transportation, and sale by color change. It can indicate the degree of quality decrease due to the temperature and time variations of a product from the time of completing fabrication until the time of utilization so as to ensure the safety of the product.

At present, such commercialized products comprise VITSAB®, Life Lines®, 3M™, DeltaTrak®, OnVu™ and so forth. Their operation principles comprise enzyme catalysis, diffusion mechanism, solid-state polymerization, etc. These products have disadvantages of inconvenience in usage and high cost. Therefore, developing a novel apparatus for indicating the passage of time is required to fulfill usage convenience, precise indication, and low cost.

SUMMARY OF THE INVENTION

In light of the above mentioned background, the present invention provides an apparatus for indicating the passage of time, composition and forming method thereof to overcome the above disadvantages in the prior art.

One object of the present invention is to indicate the passage of time by the hue change or the color density change of an indicating layer, where the reduced form and the oxidized form of a redox compound in the indicating layer have different hues and color densities. As the contact time of the reduced form of the redox compound in the indicating layer contacting with oxygen in environment increases, the amount of the oxidized form is increased so as to cause the color change effect of the indicating layer.

Another object of the present invention is to provide a composition to indicate the passage of time, comprising the redox compound and at least one photopolymerizable monomer or oligomer. The composition is coated on a substrate. By a light radiation procedure, the photopolymerizable monomer or oligomer is cured and the oxidized form of the redox compound is transformed into the reduced form. Therefore, the invention does have the economic advantages for industrial applications.

Accordingly, the present invention discloses an apparatus for indicating the passage of time, comprising a substrate and an indicating layer formed on the substrate. The indicating layer comprises a polymer matrix and a predetermined amount of the reduced form of a redox compound. The redox compound is dispersed in the polymer matrix and has the following properties: the reduced form of the redox compound reacts with oxygen to form the oxidized form of the redox compound; the hue or color density of the reduced form of the redox compound is different from that of the oxidized form of the redox compound; and the hue or color density of the indicating layer varies as the time for the reduced form of the redox compound contacting with oxygen in environment increases to have the amount of the oxidized form of the redox compound increase so as to indicate the passage of time.

BRIEF DESCRIPTION OF THE DRAWINGS

FIG. 2 shows the color change result of the apparatus for indicating the passage of time having HEMA and TCDDA with different relative ratios to change with time according to the third example of the invention.

DESCRIPTION OF THE PREFERRED EMBODIMENTS

Figure 1A:
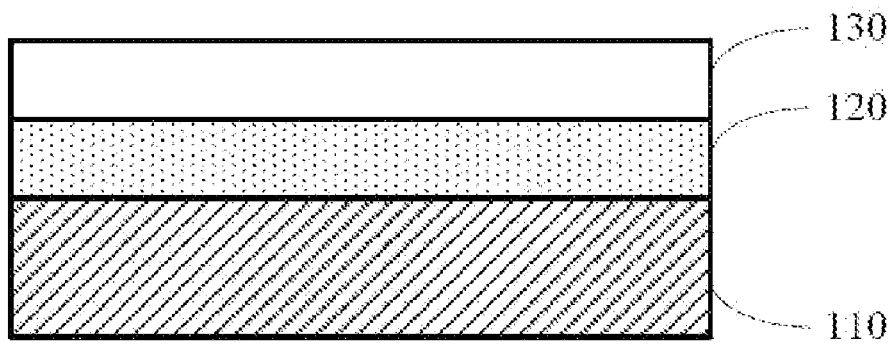
FIG. 1A shows a schematic diagram illustrating the structure of the apparatus for indicating the passage of time according to a first embodiment of the invention.

What is probed into the invention is an apparatus for indicating the passage of time and forming method thereof. Detail descriptions of the processes and elements will be provided in the following in order to make the invention thoroughly understood. Obviously, the application of the invention is not confined to specific details familiar to those who are skilled in the art. On the other hand, the common processes and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, an apparatus for indicating the passage of time is disclosed. The apparatus comprises a substrate and an indicating layer formed on the substrate. The substrate comprises one substance selected from the group consisting of the following: ceramics, metals, plastics, papers, fibers. The indicating layer comprises a polymer matrix and a predetermined amount of redox compound under the reduced form. The oxidized form can be transformed to the reduced form by light radiation. The redox compound is dispersed in the polymer matrix. In addition, the redox compound has the following properties: the reduced form of the redox compound reacts with oxygen to form the oxidized form of the redox compound; the hue or color density of the reduced form of the redox compound is different from that of the oxidized form of the redox compound; and the hue or color density of the indicating layer varies as the time for the reduced form of the redox compound contacting with oxygen in environment increases to have the amount of the oxidized form of the redox compound increase so as to indicate the passage of time.

In this embodiment, the thickness of the indicating layer is smaller than or equal to 1000 µm. Preferably, it is smaller than or equal to 300 µm. Besides, the preferred material of the polymer matrix is photopolymerizable polymer and comprises one substance selected from the group consisting of the following: acrylics, epoxy resins, polycarbonates, polyesters, polyurethanes, polyolefins, silicones and siloxanes. In a preferred example of this embodiment, because the redox compound is hydrophilic, the polymer matrix is formed by polymerization of at least one hydrophilic monomer or copolymerization of at least one hydrophilic monomer and other hydrophobic monomers, in order to have the redox compound uniformly dispersed in the polymer matrix.

In another preferred example of this embodiment, the polymer matrix is polyacrylate and formed by polymerization of an acrylate monomer with at least one polar moiety and other acrylate monomer without any polar moiety. The above polar moiety comprises one moiety selected from the group consisting of the following: hydroxyl moiety, ether moiety, amino moiety, and ketone moiety. The acrylate monomer with at least one polar moiety comprises one compound selected from the group consisting of the following: 2-hydroxyethyl methacrylate (HEMA), hydroxyethyl acrylate (HEA), hydroxypropyl acrylate (HPA), methoxy polyethylene glycol monoacrylate (MPEGMA), methoxy polyethylene glycol monomethacrylate (MPEGMMA).

Other acrylate monomer without any hydroxyl group, categorized by the number of the included double-bonds, includes the acrylate monomer with one double-bond and the acrylate monomer with a plurality of double-bonds. The acrylate monomer with one double-bond comprises one compound selected from the group consisting of the following: methyl acrylate, ethyl acrylate, butyl acrylate, octyl acrylate, methyl methacrylate, ethyl methacrylate, butyl methacrylate, isobutyl methacrylate, dimethylaminoethyl methacrylate, styrene, vinyl acetate, isobornyl methacrylate (IBMA), and any combination thereof. The acrylate monomer with a plurality of double-bonds comprises one compound selected from the group consisting of the following: ethylene glycol dimethacrylate (EGDMA), 1,3 butylene glycol dimethacrylate (BGDMA), propoxylated(2)neopentyl glycol diacrylate (PONPGDA), tricyclodecane dimethanol diacrylate (TCDDA), hydroxypivalaldehyde modified trimethylolpropane diacrylate (HTPDA), 1,4-butane diol diacrylate (BDDA), 1,6-hexane diol diacrylate (HDDA), hexanediol dimethacrylate (HDDMA), neopentylglycol diacrylate (NPGDA), trimethylolpropane triacrylate (TMPTA), ethoxylated(15)trimethylolpropone triacrylate [$EO_{(15)}$TMPTA], tris (2-hydroxy ethyl) isocyanurate triacrylate (TICTA).

In this embodiment, the molecular structure of the redox compound has conjugate structure and the oxidized form can be transformed to the reduced form by light radiation, such as quinine-imine compound, triarylmethane compound, anthaquinone compound, and indigo compound. In addition, the redox compound comprises one compound selected from the group consisting of the following: 2,2'-dipyridin (complex with Ru), nitro-o-phenantroline (nitroferroin, complex with $Fe^{2+}$), 1,10-phenantroline (ferroin, complex with $Fe^{2+}$), N-phenylantranyl acid (2-diphenylamin carboxylic acid), 5,6-dimethyl-1,10-phenantrolin (complex with $Fe^{2+}$), 2,2'-dipyridine (complex with $Fe^{2+}$), sodium (or barium) diphenylaminsulfonate, 3,3'-dimetoxybenzidine (o-dianisidine), diphenylamine, diphenylbenzidine, n-ethoxychrysoidin, variamine blue, indiamine, 2,6-dibromindophenol (2,6-dibromobenzol indophenol, Na-salt), 2,6-dichlorindophenol (2,6-dichlorbenzol indophenol, Na-salt), o-cresolindophenol (Na-salt).

Referring to FIG. 1A, in a better example of this embodiment, the apparatus for indicating the passage of time comprises a substrate 110, an indicating layer 120 formed on the substrate 110, and a protecting layer 130 formed on the indicating layer 120. The protecting layer 130 is semi-transparent or transparent, such as acrylics, epoxy resins, polycarbonates (PC), polyesters (such as PET), polyurethane, polyolefins, silicones and siloxanes. Preferably, the material of the protecting layer 130 is photopolymerizable polymer. The protecting layer is used to prevent the indicating layer from damage by external forces and to adjust the passage quantity of oxygen so as to adjust the time of color change of the indicating layer.

Figure 1B:
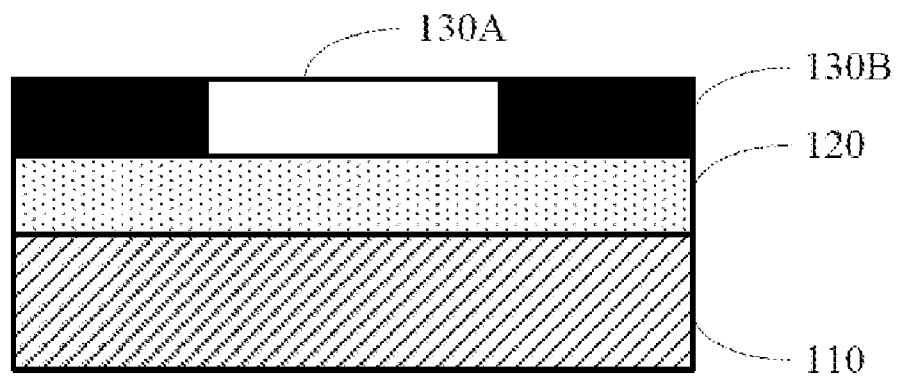
FIG. 1B shows a schematic diagram illustrating another structure of the apparatus for indicating the passage of time according to a first embodiment of the invention.

Referring to FIG. 1B, in another better example of this embodiment, the area 130B surrounding the transparent portion 130A of the protecting layer 130 has a specific color. The specific color represents a predetermined time interval. By comparing the specific color with the color of the indicating layer, it is determined whether the passage of time exceeds the predetermined time interval or not.

In practice, the apparatus for indicating the passage of time according to the invention is initially placed in a closed space. By removing the sealing material, such as sealing strip, cap, package, etc., on the outside of the closed space, the oxygen in the external environment can contact with the apparatus for indicating the passage of time according to the invention so as to start timing. As mentioned in the above, the required time interval depends on the application. Thus, a specific color can be given according to a predetermined time interval. By comparing the specific color with the color of the indicating layer, it is determined whether the passage of time exceeds the predetermined time interval or not.

In a second embodiment of the present invention, a method for forming an apparatus to indicate the passage of time is disclosed. At first, at least one photopolymerizable monomer or oligomeris and a predetermined amount of redox compound under the oxidized form are provided. The redox compound has the following properties: the reduced form of the redox compound reacts with oxygen to form the oxidized form of the redox compound; and the hue or color density of the reduced form of the redox compound is different from that of the oxidized form of the redox compound. Next, at least one photoinitiator, the at least one photopolymerizable monomer or oligomer, and the predetermined amount of redox compound are mixed until uniform to form an indicating composition. Then, the indicating composition is coated on a substrate to form an intermediate layer. The intermediate layer is irradiated by light to be cured and thereby to form an indicating layer. The apparatus for indicating the passage of time is thus formed. In the intermediate layer, the photoinitiator initiates the polymerization of the at least one photopolymerizable monomer or oligomer and the redox compound is transformed from the oxidized form to the reduced form by light radiation. The hue or color density of the indicating layer varies as the time for the reduced form of the redox compound contacting with oxygen in environment increases to have the amount of the oxidized form of the redox compound increase so as to indicate the passage of time.

In this embodiment, the photopolymerizable monomer or oligomer can be a hydrophilic monomer or oligomer or comprises at least one hydrophilic monomer or oligomer and other hydrophobic monomers or oligomers. In a preferred example of this embodiment, the photopolymerizable monomer or oligomer comprises an acrylate monomer with at least one polar moiety and other acrylate monomer without any polar moiety. The polar moiety comprises one moiety selected from the group consisting of the following: hydroxyl moiety, ether moiety, amino moiety, and ketone moiety. In addition, the selection of the acrylate monomer with at least one polar moiety, other acrylate monomer without any hydroxyl moiety, the redox compound, and the substrate is in the same manner as the first embodiment.

In the light radiation procedure, the light intensity decreases as the thickness of the intermediate layer increases. When the thickness of the intermediate layer increases up to certain degree, the lower portion that is near the substrate can not receive enough intensity of light and thus the redox compound in this portion can not be transformed from the oxidized form to the reduced form. Therefore, the thickness of the intermediate layer has to be smaller than or equal to 1000 µm, in order to ensure most of the redox compounds transformed from the oxidized form to the reduced form by the light radiation procedure. Preferably, the thickness of the indicating layer is smaller than or equal to 300 µm.

In a third embodiment of the present invention, a composition for indicating the passage of time is disclosed. The composition comprises at least one photoinitiator, at least one photopolymerizable monomer or oligomer, and a predetermined amount of redox compound under the oxidized form. The redox compound has the following properties: the reduced form of the redox compound reacts with oxygen to form the oxidized form of the redox compound; and the hue or color density of the reduced form of the redox compound is different from that of the oxidized form of the redox compound. In addition, the selection of the photopolymerizable monomer or oligomer and the redox compound is in the same manner as the first embodiment.

EXAMPLE 1

A composition for indicating the passage of time is shown in Table 1.

TABLE 1

| composition | Content (g) | Parts |
|---|---|---|
| Methylene Blue | 0.01 | 0.16 |
| Hydroxyethyl methacrylate (HEMA) | 3 | 50 |
| Tricyclodecane dimethanol diacrylate (TCDDA) | 3 | 50 |
| Photoinitiator(Ciba Irgacure 651) | 0.24 | 4 |

The composition in Table 1 is well mixed for 10 minutes to form a blue solution. Next, a 100 micron blue thin film was obtained on the glass substrate using a draw down rod. Under nitrogen environment, the blue film is converted to a colorless or yellowish film by ultraviolet light radiation. Thus, the apparatus for indicating the passage of time is formed. When the apparatus starts to contact with oxygen, color is gradually changed from colorless to blue. After 4 days, the color completely becomes blue.

EXAMPLE 2

The operating procedure is the same as that of example 1 except that the content of methylene blue in the composition varies for samples A~D shown in Table 2. In addition, the color change result for the corresponding apparatus also shown in Table 2.

TABLE 2

| | Content of MB | | color | |
|---|---|---|---|---|
| sample | (g) | parts | After UV radiation | After air oxidation |
| A | 0.005 | 0.08 | colorless | light blue |
| B | 0.02 | 0.32 | grey yellowish | grey blue |
| C | 0.01 | 0.16 | yellowish | blue |
| D | 0.03 | 0.48 | grey blue | dark blue |

EXAMPLE 3

The operating procedure is the same as that of example 1 except that the relative ratio of HEMA to TCDDA in the composition varies as shown in Table 3.

TABLE 3

| HEMA | TCDDA |
|---|---|
| 70 parts | 30 parts |
| 50 parts | 50 parts |
| 30 parts | 70 parts |

Figure 2:
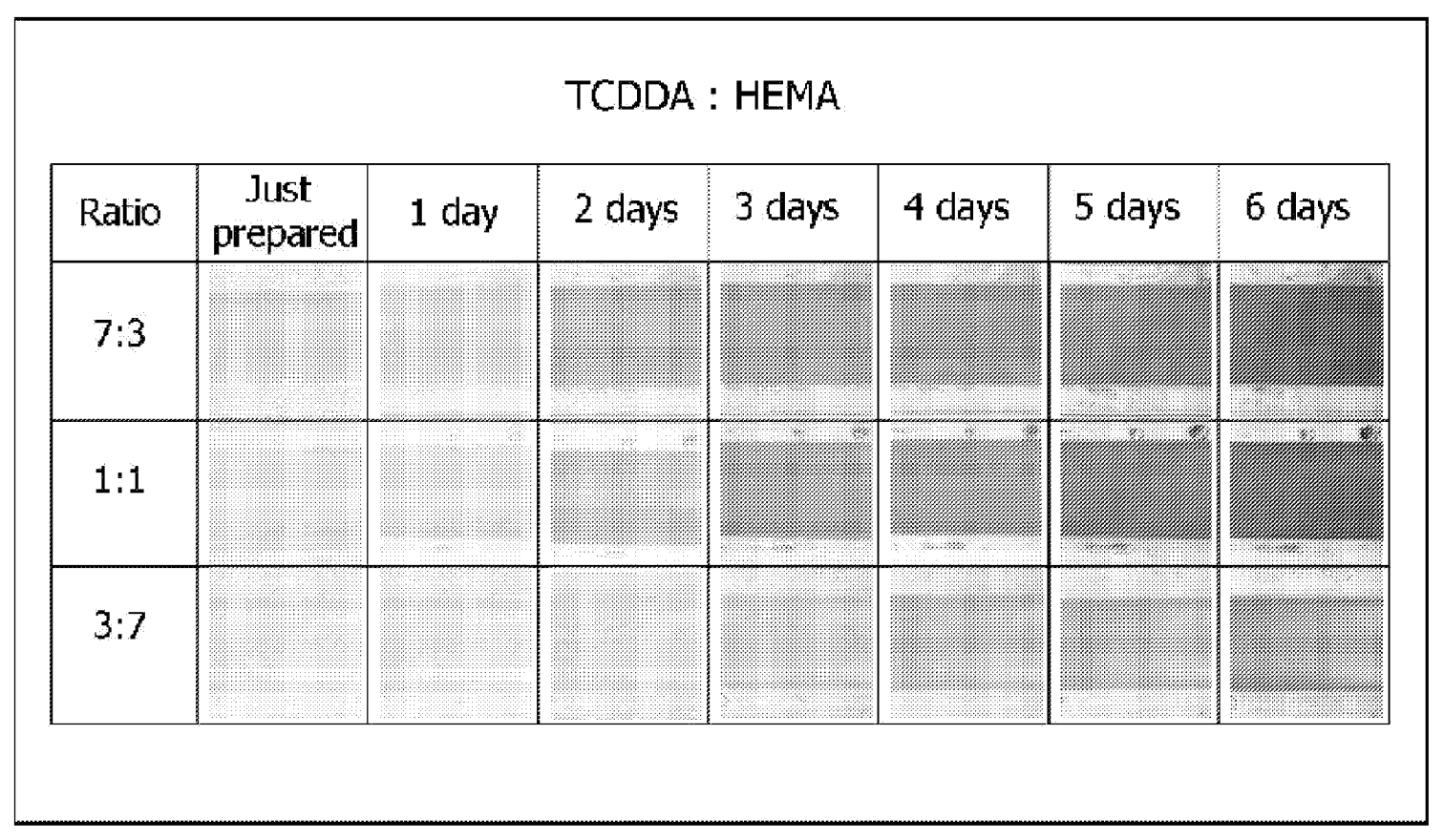

Referring to FIG. 2, when the composition has 70 parts of TCDDA, the rate of color change is very fast, i.e. it takes about 3 days for complete color change. When the ratio of HEMA to TCDDA (hydrophilic and hydrophobic acrylates) is 1:1, it takes about 4 days for complete color change. When the content of HEMA increases to 70 parts, the rate of color change is even slower, i.e. it does not completely change color even for 6 days.

EXAMPLE 4

The operating procedure is the same as that of example 1 except that $EO_{(15)}TMPTA$ is used in the composition instead of TCDDA, as shown in Table 4. HEMA and $EO_{(15)}TMPTA$ are both hydrophilic acrylates.

TABLE 4

| | Content | |
|---|---|---|
| Composition | (g) | parts |
| Methylene Blue | 0.01 | 0.16 |
| HEMA | 3 | 50 |
| $EO_{(15)}TMPTA$ | 3 | 50 |
| Photoinitiator(Irgacure 651) | 0.24 | 4 |

The fabricated apparatus for indicating the passage of time gradually changes its color as it starts to contact with oxygen for several minutes. After 3 hours, it completely changes color.

EXAMPLE 5

Similar to example 4, TCDDA is replaced with different hydrophobic acrylates in the composition, as shown in Table 5 and the color change with time is shown in Table 5.

| Hydrophobia acrylate | After UV radiation | Time for complete color change | After air oxidation |
| --- | --- | --- | --- |
| TCDDA | yellowish | 4 days | blue |
| PONPGDA | light grey | 3 days | grey blue |
| TICTA | grey | 3 days | bright blue |
| HTPDA | grey blue | 2 days | blue |
| TMPTA | — | — | — |
| IBMA | grey blue | 2 days | sky blue |

EXAMPLE 6

The operating procedure is the same as that of example 1 except that the thickness of the film in the composition is 50, 75, 100, 150, 200, 250, and 300 µm, separately. After UV radiation, the color for the film with the thickness of 50, 75, 100, 150, and 200 µm is yellowish while the color for the thicker film (250 and 300 µm) is light grey blue. In thin films the color stops to change firstly than in thicker films. The thicker films after completely color change have more intensive color.

EXAMPLE 7

The apparatus for indicating the passage of time fabricated in example 1 is placed in different humidity conditions: relative humidity 44%, 58%, 76%, 90%, and 99%. It is found that the relative humidity does not affect the color change of the apparatus for indicating the passage of time.

EXAMPLE 8

Figure 3:
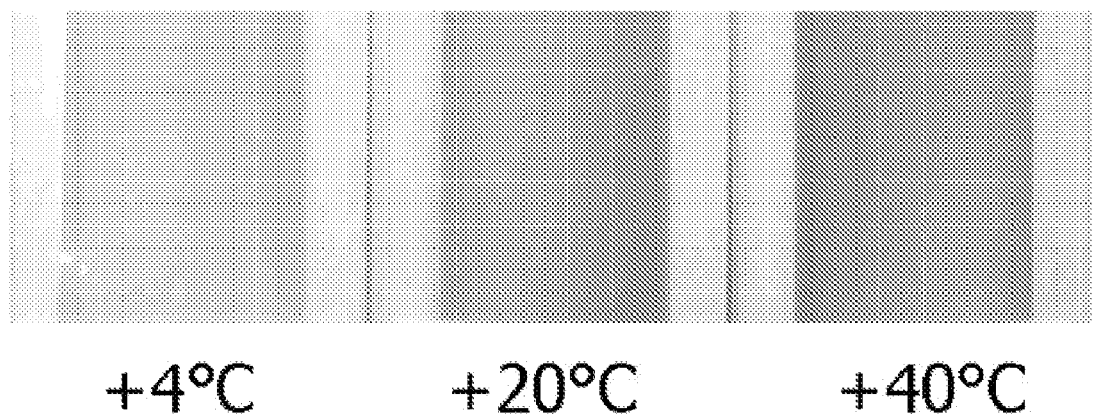
FIG. 3 shows the color change result of the apparatus for indicating the passage of time under different temperature conditions according to the eighth example of the invention.

Referring FIG. 3, the apparatus for indicating the passage of time fabricated in example 1 is placed in different temperature conditions: A (+4° C.), B (+20° C.), C (+40° C.). It is found that it takes about 5 days for A to change color completely, about 4 days for B, and about 2 days for C. As the temperature of the environment increases, the rate of color change for the apparatus increases. Besides, the final colors for sample A and sample B are the same while the final color for sample C is clearer blue. It is considered that methylene blue is well dispersed in acrylate at higher temperature.

EXAMPLE 9

The operating procedure is the same as that of example 1 except that the matrix composition in the indicating layer and the composition of the protecting layer vary. The protecting layer is formed by the reaction of different acrylates with 4% of photoinitiator (Irgacure 651) and has a thickness of 100 µm. The color change conditions of the different apparatuses and time are shown in Table 6.

TABLE 6

| Matrix composition of indicating layer | Composition for protecting layer | color After UV radiation | After air oxidation | Time for complete color change |
| --- | --- | --- | --- | --- |
| TCDDA/HEMA | — | colorless | blue | 4 days |
| TCDDA/HEMA | TICTA | colorless | grey blue | 5 days |
| TCDDA/HEMA | IBMA | colorless | blue | 4 days |
| TCDDA/HEMA | PONPGDA | colorless | blue | 4 days |
| TCDDA/HEMA | TCDDA/HEMA | colorless | grey blue | 5 days |
| TCDDA/HEMA | TCDDA | colorless | blue | 6-7 days |
| TICTA/HEMA | TCDDA | grey | purple | 5 days |
| EO(15)TMPTA/HEMA | — | colorless | blue | 3 hrs |
| EO(15)TMPTA/HEMA | PONPGDA | colorless | blue | 3 days |
| EO(15)TMPTA/HEMA | IBMA | colorless | blue | 3 days |
| EO(15)TMPTA/HEMA | TICTA | colorless | purple | 1-2 days |
| EO(15)TMPTA/HEMA | TCDDA | colorless | purple | 4 days |

In the embodiment of the invention, the invention uses the property of the hue or color density difference between the reduced form and the oxidized form of the redox compound to change the hue or color density of the indicating layer so as to indicate the passage of time. As the time for the reduced form of the redox compound contacting with oxygen increases, the quantity of the oxidized form of the redox compound increases so as to cause the indicating layer to change. On the other hand, the invention provides the composition to indicate the passage of time, comprising the redox compound and at least one photopolymerizable monomer or oligomer. The composition is coated on a substrate. By a light radiation procedure, the photopolymerizable monomer or oligomer is cured and the oxidized form of the redox compound is transformed into the reduced form. Therefore, the invention does have the economic advantages for industrial applications.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An apparatus for indicating the passage of time, comprising:
    a substrate comprising one substance selected from the group consisting of the following: ceramics, metals, plastics, papers, fibers; and
    an indicating layer formed on said substrate, having a thickness smaller than or equal to 1000 µm, and comprising a polymer matrix and a predetermined amount of redox compound under the reduced form;
    wherein said redox compound is transformed from the oxidized form to the reduced form by light radiation treatment and said redox compound is dispersed in said polymer matrix and has the following properties: the reduced form of said redox compound reacts with oxygen to form the oxidized form of said redox compound; the hue or color density of the reduced form of said redox compound is different from that of the oxidized form of said redox compound; the hue or color density of said indicating layer varies as the time for the reduced form of said redox compound contacting with oxygen in environment increases to have the amount of the oxidized form of said redox compound increase so as to indicate the passage of time; and said polymer matrix is a photopolymerizable polymer matrix comprising one substance selected from the group consisting of the following: acrylics, epoxy resins, polycarbonates, polyesters, polyurethane, polyolefins, silicones and siloxanes.

2. The apparatus according to claim 1, wherein the thickness of said indicating layer is smaller than or equal to 300 μm.

3. The apparatus according to claim 1, wherein said polymer matrix is formed by polymerization of at least one hydrophilic monomer or copolymerization of at least one hydrophilic monomer and other hydrophobic monomers.

4. The apparatus according to claim 1, wherein said polymer matrix is polyacrylate and formed by polymerization of an acrylate monomer with at least one polar moiety and other acrylate monomer without any polar moiety.

5. The apparatus according to claim 4, wherein said polar moiety comprises one moiety selected from the group consisting of the following: hydroxyl moiety, ether moiety, amino moiety, and ketone moiety.

6. The apparatus according to claim 1, wherein said redox compound comprises one compound selected from the group consisting of the following: quinine-imine compound, triarylmethane compound, anthraquinone compound, and indigo compound.

7. The apparatus according to claim 1, further comprising: a protecting layer formed on said indicating layer wherein at least one portion of said protecting layer is transparent for observation of the color change of said indicating layer from outside.

8. The apparatus according to claim 7, wherein the transparent portion of said protecting layer is surrounded by an area with a specific color representing a predetermined time interval and comparing the specific color with the color of said indicating layer is used to determined whether the passage of time exceeds the predetermined time interval or not.

9. A method for forming an apparatus to indicate the passage of time, comprising:
providing at least one photopolymerizable monomer or oligomer;
providing a predetermined amount of redox compound under the oxidized form wherein said redox compound has the following properties: the reduced form of said redox compound reacts with oxygen to form the oxidized form of said redox compound; the hue or color density of the reduced form of said redox compound is different from that of the oxidized form of said redox compound;
mixing at least one photoinitiator, said at least one photopolymerizable monomer or oligomer and said predetermined amount of redox compound until uniform to form an indicating composition;
coating said indicating composition on a substrate to form an intermediate layer wherein said substrate comprises one substance selected from the group consisting of the following: ceramics, metals, plastics, papers, fibers; and said intermediate layer has a thickness smaller than or equal to 1000 μm; and
performing a light radiation procedure for said intermediate layer to cure and form an indicating layer so as to form said apparatus to indicate the passage of time;
wherein in said intermediate layer, said photoinitiator initiates the polymerization of said at least one photopolymerizable monomer or oligomer and said redox compound is transformed from the oxidized form to the reduced form by light radiation; and the hue or color density of said indicating layer varies as the time for the reduced form of said redox compound contacting with oxygen in environment increases to have the amount of the oxidized form of said redox compound increase so as to indicate the passage of time.

10. The method according to claim 9, wherein said photopolymerizable monomer or oligomer is a hydrophilic monomer or oligomer.

11. The method according to claim 9, wherein said at least one photopolymerizable monomer or oligomer comprises at least one hydrophilic monomer or oligomer and other hydrophobic hydrophilic monomer or oligomer.

12. The method according to claim 9, wherein said at least one photopolymerizable monomer or oligomer comprises an acrylate monomer with at least one polar moiety and other acrylate monomer without any polar moiety.

13. The method according to claim 12, wherein said polar moiety comprises one moiety selected from the group consisting of the following: hydroxyl moiety, ether moiety, amino moiety, and ketone moiety.

14. The method according to claim 9, wherein said redox compound comprises one compound selected from the group consisting of the following: quinine-imine compound, triarylmethane compound, anthraquinone compound, and indigo compound.

15. The method according to claim 9, wherein the thickness of said intermediate layer is smaller than or equal to 300 μm.

16. A composition for indicating the passage of time, comprising:
at least one photoinitiator;
at least one photopolymerizable monomer or oligomer; and
a predetermined amount of redox compound under the oxidized form wherein said redox compound has the following properties: the reduced form of said redox compound reacts with oxygen to form the oxidized form of said redox compound; the hue or color density of the reduced form of said redox compound is different from that of the oxidized form of said redox compound.

17. The composition according to claim 16, wherein said photopolymerizable monomer or oligomer is a hydrophilic monomer or oligomer.

18. The composition according to claim 16, wherein said at least one photopolymerizable monomer or oligomer comprises at least one hydrophilic monomer or oligomer and other hydrophobic monomer or oligomer and the duration of the redox compound changing from the reduced form to the oxidized form depends on the molar ratio of the hydrophilic monomer or oligomer to the hydrophobic monomer or oligomer.

19. The composition according to claim 16, wherein said at least one photopolymerizable monomer or oligomer comprises an acrylate monomer with at least one polar moiety and other acrylate monomer without any polar moiety.

20. The composition according to claim 19, wherein said polar moiety comprises one moiety selected from the group consisting of the following: hydroxyl moiety, ether moiety, amino moiety, and ketone moiety.

21. The composition according to claim 16, wherein said redox compound comprises one compound selected from the group consisting of the following: quinine-imine compound, triarylmethane compound, anthraquinone compound, and indigo compound.

* * * * *